United States Patent
McCauley

(10) Patent No.: US 10,184,922 B2
(45) Date of Patent: Jan. 22, 2019

(54) GAS CHROMATOGRAPHY COLUMNS WITH INTEGRATED FERRULES

(71) Applicant: Thermo Finnigan LLC, San Jose, CA (US)

(72) Inventor: Edward B. McCauley, Cedar Park, TX (US)

(73) Assignee: Thermo Finnigan LLC, San Jose, CA (US)

( * ) Notice: Subject to any disclaimer, the term of this patent is extended or adjusted under 35 U.S.C. 154(b) by 368 days.

(21) Appl. No.: 15/083,678

(22) Filed: Mar. 29, 2016

(65) Prior Publication Data

US 2017/0282113 A1   Oct. 5, 2017

(51) Int. Cl.
*G01N 30/60* (2006.01)
*B01D 53/02* (2006.01)
*C09D 179/08* (2006.01)

(52) U.S. Cl.
CPC ....... *G01N 30/6026* (2013.01); *B01D 53/025* (2013.01); *C09D 179/08* (2013.01); *G01N 30/6078* (2013.01); *B01D 2253/202* (2013.01)

(58) Field of Classification Search
CPC ............ B01D 53/025; G01N 30/6026; G01N 30/6034; G01N 30/6039; G01N 30/6052; G01N 30/6073; G01N 30/6078
See application file for complete search history.

(56) References Cited

U.S. PATENT DOCUMENTS

| | | | | |
|---|---|---|---|---|
| 5,938,919 A | * | 8/1999 | Najafabadi | G01N 30/6047 210/198.2 |
| 8,128,131 B2 | | 3/2012 | Barnett et al. | |
| 2005/0041931 A1 | * | 2/2005 | Lampert | G02B 6/3859 385/81 |
| 2007/0000828 A1 | * | 1/2007 | Norman | G01N 30/72 210/198.2 |
| 2007/0003447 A1 | * | 1/2007 | Gleason | B01L 3/0268 422/504 |
| 2012/0169040 A1 | * | 7/2012 | Barnett | F16L 7/02 285/24 |
| 2015/0260694 A1 | * | 9/2015 | Matsuoka | G01N 30/30 73/23.41 |

* cited by examiner

*Primary Examiner* — Robert Clemente
(74) *Attorney, Agent, or Firm* — David A. Schell

(57) ABSTRACT

A capillary column includes a fused silica tubing and a polyimide coating over the fusing silica tubing. Additionally, the capillary column further includes a first plurality of integrated ferrules positioned along at least a first portion of the fused silica tubing and spaced apart from one another by a first fixed interval.

20 Claims, 2 Drawing Sheets

GAS CHROMATOGRAPHY COLUMNS WITH INTEGRATED FERRULES

FIELD

The present disclosure generally relates to the field of gas chromatography including gas chromatography columns with integrated ferrules.

INTRODUCTION

Gas chromatography (GC) is used for separating and analyzing compounds that can be vaporized without decomposition. GC can be used to test the purity of a particular substance, separate the different components of a mixture, determine the relative amounts of different components of a mixture, and the like. In gas chromatography, the mobile phase (or "moving phase") is a carrier gas, usually an inert gas such as helium or an unreactive gas such as nitrogen. The stationary phase is a layer of liquid or polymer on an inert solid support, inside a column, generally a piece of glass or metal tubing.

The gaseous compounds being analyzed interact with the stationary phase coated on the inner wall of the column. Due to differences in the degree of interaction between the stationary phase and each compound, compounds can elute at a different time, known as the retention time of the compound. The retention time can be a function of the compound, the stationary phase, the carrier gas flow rate, the temperature, the length of the column, and other factors.

When a column is of insufficient length, there may be inadequate separation between compounds due to the difference in retention times being too small. However, it can periodically become necessary to trim the end of the column (particularly the end adjacent to the sample injector) due to non volatile matrix residuals that become trapped within the first few inches of the column. For example, highly polar compounds that interact so strongly with the stationary phase as to become substantially immobile can become trapped within the initial portion of the column. These trapped compounds can result in poor chromatographic peak shapes, undesirable shifts in retention times and poor quantitation of targeted compounds. Trimming the column can re-establish good chromatography, yet it presents several challenges. First, positioning the ferrule at an appropriate length to ensure the end of the column is inserted through an aperture to the right distance can require multiple measurements to position the ferrule and to confirm the ferrule has not moved during the process. Second, contamination can be introduced if a marking fluid or adhesive tape is used on the column as a visual aid for proper positioning. Third, it can be a tedious endeavor to thread the tiny bore column through a small ferrule in the relatively dark confines of a GC oven without proper eyesight, lighting, or magnification tools. Fourth, it is problematic to track the remaining length of column to correct for changes in retention time as well as to know when the column needs to be replaced due to the remaining column being too short.

From the foregoing it will be appreciated that a need exists for improvements in gas chromatography columns.

SUMMARY

In a first aspect, a capillary column can include a fused silica tubing, a polyimide coating over the fusing silica tubing, and a first plurality of integrated ferrules positioned along at least a first portion of the fused silica tubing and spaced apart from one another by a first fixed interval.

In embodiments of the first aspect, the first fixed interval can be not less than an insertion depth.

In embodiments of the first aspect, the first plurality of integrated ferrules can be oriented in a first direction and first portion of the fused silica tubing can be located at or near a first end of the capillary column. The capillary column can further comprise a second plurality of integrated ferrules positioned along a second portion of the fused silica tubing and spaced apart from one another by a second fixed interval. The second portion of the fused silica tubing can be located at or near a second end of the capillary column. In particular embodiments, the first fixed interval can be greater than the second fixed interval.

In embodiments of the first aspect, the plurality of integrated ferrules can include graphite, polyimide, or a combination thereof. In particular embodiments, the plurality of integrated ferrules can be cemented to the polyimide coating.

In embodiments of the first aspect, the plurality of integrated ferrules can include a metal. In particular embodiments, the plurality of integrated ferrules can be pre-swaged to the capillary column.

In a second aspect, a method of manufacturing a capillary column can include obtaining a polyimide coated fused silica tubing, and affixing a plurality of ferrules to the polyimide coated fused at a fixed interval from one another.

In embodiments of the second aspect, obtaining the polyimide coated fused silica tubing can include forming a fused silica tubing, and coating the fused silica tubing with one or more layers of polyimide.

In embodiments of the second aspect, the fixed interval can be not less than an insertion depth.

In embodiments of the second aspect, affixing the plurality of ferrules can include pre-swaging the ferrules or cementing the ferrules in place.

In embodiments of the second aspect, affixing the plurality of ferrules can include forming the ferrules in place.

In embodiments of the second aspect, the plurality of integrated ferrules can include graphite, polyimide, or a combination thereof.

In embodiments of the second aspect, the plurality of integrated ferrules can include a metal.

In a third aspect, a capillary column can include a plurality of integrated ferrules positioned along at least a portion of the capillary column and spaced apart by a fixed length. The plurality of integrated ferrules can include a first ferrule and a second ferrule. A method of using a capillary column can include unscrewing a nut securing the capillary column at the first ferrule, removing an end of the capillary column from an instrument, and trimming the capillary column to remove an end portion including the first ferrule and leaving the second ferrule spaced from the end of the capillary column by a predetermined length of capillary column. The method can further include inserting the pre-determine length of capillary column into an opening of the instrument, and securing the capillary column in place with the nut.

In embodiments of the second aspect, the plurality of integrated ferrules can include graphite, polyimide, or a combination thereof. In particular embodiments, the plurality of integrated ferrules can be cemented to the polyimide coating.

In embodiments of the second aspect, the plurality of integrated ferrules can include a metal. In particular embodiments, the plurality of integrated ferrules can be pre-swaged to the capillary column.

DRAWINGS

For a more complete understanding of the principles disclosed herein, and the advantages thereof, reference is now made to the following descriptions taken in conjunction with the accompanying drawings, in which.

Figure 1:
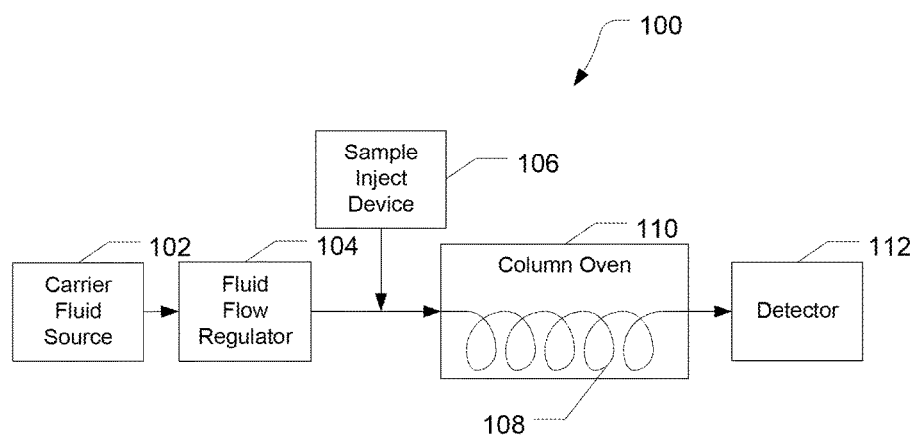
FIG. 1 is a block diagram of an exemplary gas chromatography system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of gas chromatography columns are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Gas Chromatography Systems

Various embodiments of gas chromatography system 100 can include components as displayed in the block diagram of FIG. 1. In various embodiments, elements of FIG. 1 can be incorporated into gas chromatography system 100. According to various embodiments, gas chromatography system 100 can include a carrier fluid source 102, a fluid flow regulator 104, a sample inject device 106, a column 108, a column oven 110, and a detector 112.

In various embodiments, the carrier fluid source 102 provides a carrier fluid to the chromatography system 100. The carrier fluid can typically be a gas, such as helium, nitrogen, argon, hydrogen, air, or any combination thereof.

In various embodiments, the fluid flow regulator 104 regulates a flow of the carrier fluid through the gas chromatography system 100. The carrier gas transports a sample into and through the column 108. The carrier gas linear velocity can affect the analysis with a higher linear velocity resulting in a faster analysis, but lower separation between analytes.

Early GCs used chromatographic columns loosely packed with diatomaceous earth substrates coated with a certain percentage of stationary phase liquid. These early GC columns typically consumed 30 sccm of carrier gas or more, and were constructed of all glass tubing having a typical length of one or two meters and an internal diameter of 2 to 6 millimeters. Flow in these columns was controlled using mechanical flow controllers designed to keep a constant flow rate independent of the column back pressure. This is advantageous when employing detectors sensitive to the column effluent flow rate. When the stationary phase of these columns became contaminated with non volatile matrix deposits, it was necessary to re-pack at least the initial portion of these columns in order to re-establish chromatographic performance. It was not practical to trim these columns to remove the contaminated portion of the stationary phase, since the columns were generally all glass construction. Doing so would result in the inability to reconnect the column with injector and detector ports as well as result in significant changes in retention times and separating power. Conversely, with the introduction of wall coated open tubular fused silica capillary GC columns having much greater length, replacing the stationary phase became impractical; yet trimming the column became possible due to the inherent flexibility of fused silica and the long relative lengths of these types of columns. Trimming can be employed to restore chromatographic performance without undue loss in separation power, since capillary columns are generally tens of meters in length, while only a few tens of centimeters are required to trim such columns in order to restore performance. Mechanical flow controllers were no longer suitable on these columns due to the far lower flow rates employed. A typical open tube capillary column consumes only a few standard cubic centimeters per minute which is difficult to regulate with mechanical type flow controllers. Instead, the column flow rate is controlled indirectly using an applied pressure according to the well known Poiseuille equation.

$$\frac{dV}{dT} = \frac{\pi r^4}{16\eta L}\left(\frac{(p_i^2 - p_o^2)}{p_0}\right) \quad \text{Equation 1}$$

where:
  $P_i$ inlet pressure
  $P_o$ outlet pressure
  L is the length of the column
  η is the viscosity of the gas (a function of temperature)
  r is the column internal radius Modern GC's electronically control the carrier gas pressure in accordance with equation 1. Consequently, carrier pressures and flow rates can be adjusted during the run under a closed loop computer algorithm, creating pressure and or flow programs similar to temperature programs. As can be seen in equation 1, the column internal diameter as well as the column length is required for proper flow control of carrier gas in these systems. As a capillary column is routinely trimmed, the new column length needs to be entered into the control program of the chromatograph. Additionally, if a column is to be removed from a chromatograph for storage and later use, a logbook needs to be established linking the serial number of the column to its present length, since no visual aid is present which indicates the remaining length of column.

In various embodiments, the sample inject device 106 can be used to load or inject a sample into the system 100. The sample inject device 106 can be heated vaporize the sample so it can be carried into the column 108 by the carrier gas. The sample inject device 106 can be a split/splitless injector enabling the user to choose between injecting the entire sample (useful for small or dilute samples) or dilute the sample with the carrier gas (useful for concentrated samples).

In various embodiments, the column 108 is generally a fused silica or metallic capillary column with a stationary compound coating the inner surface. Common stationary phases in open tubular columns are cyanopropylphenyl dimethyl polysiloxane, carbowax polyethyleneglycol, bis-cyanopropyl cyanopropylphenyl polysiloxane and diphenyl dimethyl polysiloxane.

In various embodiments, the column oven 110 can control the temperature of the column 108. The temperature of oven 110 can be precisely controlled electronically.

The rate at which a sample passes through the column can be directly proportional to the temperature of the column. The higher the column temperature, the faster the sample can move through the column. However, the faster a sample moves through the column, the less time it has to interact with the stationary phase, resulting in less separation between components of the sample. In general, the column temperature is often selected as a compromise between the length of the analysis and the degree of separation.

In various embodiments, the temperature may be held constant throughout the analysis (isothermal separation). In other embodiments, the temperature can be varied (generally increasing) throughout the run. By controlling and adjusting the initial temperature and the rate of increase, adequate separation can be achieved for certain compounds while decreasing the overall run time by sacrificing separation in other parts of the run.

In various embodiments, the detector 112 can detect components of the sample as they exit the column, and correlate the measurement with a retention time. Numerous detectors can be incorporated, including flame ionization detectors (FID), thermal conductivity detectors (TCD), catalytic combustion detectors (CCD), discharge ionization detectors (DID), electron capture detectors (ECD), flame photometric detectors (FPD), Infrared detectors (IRD), mass spectrometers (MS), vacuum ultraviolet detectors (VUV), and the like.

Figure 2:
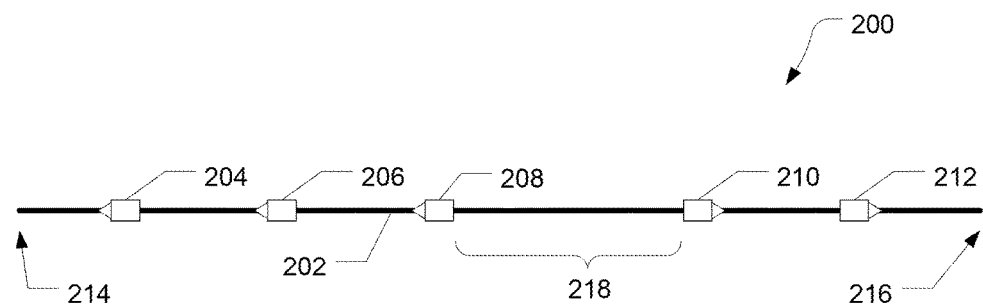
FIG. 2 is a schematic diagram of an exemplary gas chromatography column with integrated ferrules, in accordance with various embodiments.

FIG. 2 is a diagram 200 depicting a GC column 202 with integrated ferrules 204, 206, 208, 210, and 212. Column 202 can be a fused silica column with a polymer coating on the outer surface of the column. In various embodiments, the polymer coating can be a polyimide coating. Alternatively, column 202 can be a metal column. The inner surface of the column can include a stationary phase appropriate for GC separation of compounds.

Column 202 can include an end 214 and an end 216. Integrated ferrules 204, 206 and 208 can be located near end 214 and oriented to be used in conjunction with end 214. Integrated ferrules 210 and 212 can be located near end 216 and be oriented to be used in conjunction with end 216. For example, end 214 can be coupled to an injection port of the GC system, such as GC system 100, and end 216 can be coupled to a detector. In various embodiments, end 214 or end 216 can be inserted through an orifice with an insertion length of column extending through the orifice and a ferrule and nut used to secure the column in place and prevent leaks.

In various embodiments, integrated ferrules 204, 206, 208, 210, and 212 can include graphite, a polymer such as polyimide, or a combination thereof. Alternatively, the integrated ferrules 204, 206, 208, 210, and 212 can be formed of metal.

In various embodiments, the integrated ferrules 204, 206, 208, 210, and 212 can be fixed to the column by cementing with a polymer bonding agent, such as using a polyimide glue to adhere the integrated ferrules 204, 206, 208, 210, and 212 with a polyimide coating on column 202. In alternate embodiments, the ferrules can be pre-swaged to the column to prevent slippage.

Integrated ferrules 204, 206, and 208 can be fixed to the GC column at fixed intervals. In various embodiments, the fixed interval can be not less than the insertion depth of the column, such as when inserted into injection port. The insertion depth can be the depth necessary to insert the column through an orifice of the GC system to ensure proper leak free connectivity between the column and another component of the GC system, such as the injection port.

In various embodiments, integrated ferrules 210 and 212 can be oriented in an opposite direction than integrated ferrules 204, 206, and 208. For example, integrated ferrules can be oriented to be used in conjunction with the detector. Further, integrated ferrules 210 and 212 can be spaced apart by a fixed interval different than, such as greater than, the fixed interval used in spacing integrated ferrules 204, 206, and 208, such as when the insertion depth for coupling with the detector is different than the insertion depth for coupling with the injection port. Further, as the injection port side of the column may be more frequently trimmed than the detector side of the column, more integrated ferrules may be oriented for use with end 214.

In various embodiments, the column may include a gap 218 separating the first group of ferrules oriented in a first direction (integrated ferrules 204, 206, and 208) from the second group of ferrules orient in the second direction (integrated ferrules 210 and 212). After the last ferrule on one side of the column is used (such as ferrule 208), the column may need replacement. The length of gap may be a minimum useful column length, such that using a shorter column would result in insufficient resolution of compound.

Figure 3:
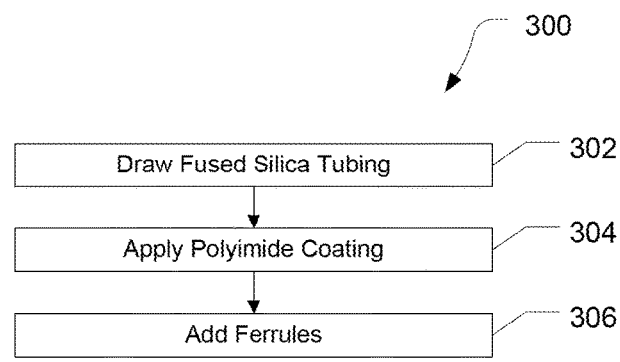
FIG. 3 is a flow diagram illustrating a method of making a gas chromatography column with integrated ferrules, in accordance with various embodiments.

FIG. 3 is a flow diagram of a method of manufacturing a column with integrated ferrules. At 302, fused silica tubing can be drawn. In various embodiments, the tubing can be continuously pulled from molten silicon dioxide, typically from a high purity fused silica pre-form. As the tubing is pulled, it can be appropriately sized, such as by controlling the inner diameter, the outer diameter, the wall thickness, or any combination thereof, and cooled to hold the size and shape.

At 304, the fused silica tubing can be coated in one or more layers of a polymer, such as polyimide. In various embodiments, the tubing can be dipped in the polymer one or more times with the polymer being allowed to polymerize or cool between dips. In particular embodiments, the tubing can be formed continuously. A continuous tube can be drawn from the molten silicon dioxide, guided through a controlled cooling/annealing zone, and through the polymer bath. The tubing may loop through a polymerizing/cooling zone and back into the polymer bath a plurality of times to provide sufficient thickness of the polymer coating.

At 306, ferrules can be added to the tubing at predetermined locations along the tubing. In various embodiments, the ferrules can include graphite, a polymer such as polyimide, or a combination thereof. Alternatively, the ferrules can be metal. The ferrules can be positioned such that they are spaced apart by a fixed interval, such as a length not less than the insertion depth necessary when the column is in use.

In various embodiments, the tubing may be cut to size and then the ferrules threaded onto the tubing and positioned before affixing the ferrules to the tubing. In various embodiments, the ferrules can be affixed by pre-swaging. In other embodiments, the ferrules can be affixed using a polymer bonding agent to bond the ferrules to the polymer coating. In yet other embodiments, the ferrules may be formed in place on the tubing, such as by molding or casting in place. In particular embodiments, the ferrules can be formed on the continuously forming tubing, such as by a two part mold coming together around the moving tubing at a beginning of a ferrule forming zone. The ferrule material can be applied within the mold, and the mold can travel with the tubing through a ferrule forming zone while the ferrule is formed. The two part mold may then be removed at the end of the ferrule forming zone to reveal an integrated ferrule and then the mold can return to the beginning of the ferrule forming zone to be reused.

Figure 4:
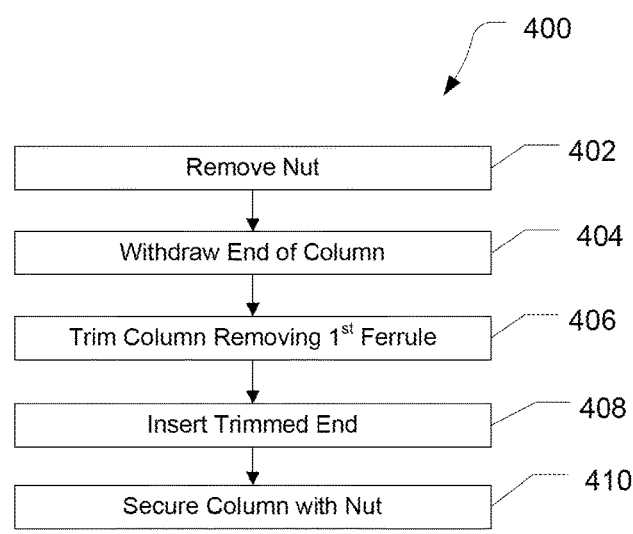
FIG. 4 is a flow diagram illustrating a method of using a gas chromatography column with integrated ferrules, in accordance with various embodiments.

FIG. 4 is a flow diagram of a method of using a column with integrated ferrules. The ferrules can include graphite, a polymer such as polyimide, or a combination thereof. Alternatively, the ferrules can be metal. The ferrules can be positioned such that they are spaced apart by a fixed interval, such as a length not less than the insertion depth necessary when the column is in use. The integrated ferrules can be affixed to the column, such as by cementing or pre-swaging.

At 402, a nut securing the column at a first ferrule can be loosened to free a first ferrule. In various embodiments, the nut can be a split nut, such that a slot on the side can be used for placing the nut around the tubing and removing the nut from the tubing to enable positioning adjacent to an appropriate integrated ferrule. In particular, after loosening the nut, the nut can be removed from the column and saved for later use.

At 404, an end of the column can be withdrawn from an orifice, and at 406, a portion of the column containing the first ferrule can be trimmed from the column. In various embodiments, the column can be trimmed to leave a length of column corresponding to an insertion depth between the new end and a second ferrule.

At 408, the new end of the column can be inserted into the orifice, up to the insertion depth, and at 410, the nut can be placed around the column and used to secure the ferrule and column within the orifice.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A capillary column comprising:
   a fused silica tubing;
   a polyimide coating over the fused silica tubing; and
   a first plurality of integrated ferrules positioned along at least a first portion of the fused silica tubing and spaced apart from one another by a first fixed interval, the first plurality of integrated ferrules are oriented in a first direction.

2. The capillary column of claim 1 wherein the first fixed interval is not less than an insertion depth.

3. The capillary column of claim 1 wherein the first portion of the fused silica tubing is located at or near a first end of the capillary column, and further comprising a second plurality of integrated ferrules positioned along a second portion of the fused silica tubing and spaced apart from one another by a second fixed interval, the second portion of the fused silica tubing located at or near a second end of the capillary column.

4. The capillary column of claim 3 wherein the first fixed interval is greater than the second fixed interval.

5. The capillary column of claim 1 wherein the plurality of integrated ferrules include graphite, polyimide, or a combination thereof.

6. The capillary column of claim 5 wherein the plurality of integrated ferrules are cemented to the polyimide coating.

7. The capillary column of claim 1 wherein the plurality of integrated ferrules include a metal.

8. The capillary column of claim 7 wherein the plurality of integrated ferrules are pre-swaged to the capillary column.

9. A method of manufacturing a capillary column, comprising:

obtaining a polyimide coated fused silica tubing; and affixing a plurality of ferrules to the polyimide coated fused silica tubing at a fixed interval from one another and oriented in a first direction.

10. The method of claim 9 wherein obtaining the polyimide coated fused silica tubing includes:

forming a fused silica tubing; and coating the fused silica tubing with one or more layers of polyimide.

11. The method of claim 9 wherein the fixed interval is not less than an insertion depth.

12. The method of claim 9 wherein affixing the plurality of ferrules includes pre-swaging the ferrules or cementing the ferrules in place.

13. The method of claim 9 wherein affixing the plurality of ferrules includes forming the ferrules in place.

14. The method of claim 9 wherein the plurality of integrated ferrules include graphite, polyimide, or a combination thereof.

15. The method of claim 9 wherein the plurality of integrated ferrules include a metal.

16. A method of using a capillary column, the capillary column including a plurality of integrated ferrules positioned along at least a portion of the capillary column and spaced apart by a fixed length, the plurality of integrated ferrules including a first ferrule and a second ferrule, the method comprising:

unscrewing a nut securing the capillary column at the first ferrule;

removing an end of the capillary column from an instrument;

trimming the capillary column to remove an end portion including the first ferrule and leaving the second ferrule spaced from the end of the capillary column by a predetermined length of capillary column;

inserting the predetermine length of capillary column into an opening of the instrument; and securing the capillary column in place with the nut.

17. The method of claim 16 wherein the plurality of integrated ferrules include graphite, polyimide, or a combination thereof.

18. The method of claim 17 wherein the plurality of integrated ferrules are cemented to the polyimide coating.

19. The method of claim 16 wherein the plurality of integrated ferrules include a metal.

20. The method of claim 19 wherein the plurality of integrated ferrules are pre-swaged to the capillary column.

* * * * *